US011559340B2

(12) United States Patent
Fell et al.

(10) Patent No.: US 11,559,340 B2
(45) Date of Patent: Jan. 24, 2023

(54) BONE REPAIR SYSTEM AND METHOD

(71) Applicants: The Penn State Research Foundation, University Park, PA (US); Barry M. Fell, Hummelstown, PA (US)

(72) Inventors: Barry M. Fell, Hummelstown, PA (US); Peter W. Dillon, Harrisburg, PA (US); Donald R. MacKay, Hershey, PA (US); Randy S. Haluck, Lititz, PA (US)

(73) Assignee: The Penn State Research Foundation, University Park, PA (US)

( * ) Notice: Subject to any disclaimer, the term of this patent is extended or adjusted under 35 U.S.C. 154(b) by 566 days.

(21) Appl. No.: 16/713,532

(22) Filed: Dec. 13, 2019

(65) Prior Publication Data
US 2020/0113611 A1 Apr. 16, 2020

Related U.S. Application Data

(60) Division of application No. 15/433,499, filed on Feb. 15, 2017, now Pat. No. 10,537,372, which is a
(Continued)

(51) Int. Cl.
*A61B 17/80* (2006.01)
*A61B 17/84* (2006.01)
(Continued)

(52) U.S. Cl.
CPC ...... *A61B 17/8076* (2013.01); *A61B 17/1792* (2016.11); *A61B 17/3468* (2013.01);
(Continued)

(58) Field of Classification Search
CPC .............. A61B 17/8869; A61B 17/842; A61B 17/8076; A61B 17/823; A61B 17/8861
See application file for complete search history.

(56) References Cited

U.S. PATENT DOCUMENTS 2,143,922 A * 1/1939 Longfellow ......... A61B 17/683
606/59
3,709,219 A 1/1973 Halloran
(Continued)

FOREIGN PATENT DOCUMENTS

CA 2361282 A1 3/2003
CN 201617934 U 11/2010

OTHER PUBLICATIONS

Acute Innovations, BioBridge, Resorbable Chest Wall Stabilization Plate brochure, Nov. 2010, pp. 1-3.
(Continued)

*Primary Examiner* — David W Bates
(74) *Attorney, Agent, or Firm* — Brooks Kushman P.C.

(57) ABSTRACT

A bone repair system and method for percutaneously fixing a first bone segment to a second bone segment, such as rib bone segments, in a body of a patient include drilling a first hole through the first bone segment and a second hole through the second bone segment, and feeding a first tether through the first hole and a second tether through the second hole, each tether having a proximal end and a distal end. The first and second tether distal ends are withdrawn from the body while the first and second tether proximal ends have not passed through the first and second bone segments, respectively. A reinforcing member, such as a bone plate, having first and second openings, is passed onto the first and second tether distal ends, and the reinforcing member is pulled into engagement with the first and second bone segments guided by the tethers. The reinforcing member is secured to the first bone segment with a first fastener assembly through the first hole and the first opening and to the second bone segment with a second fastener assembly through the second hole and the second opening to fix the first bone segment to the second bone segment.

14 Claims, 11 Drawing Sheets

Related U.S. Application Data continuation of application No. 14/252,064, filed on Apr. 14, 2014, now Pat. No. 9,603,642, which is a division of application No. 12/825,967, filed on Jun. 29, 2010, now Pat. No. 8,728,133.

(60) Provisional application No. 61/221,744, filed on Jun. 30, 2009, provisional application No. 61/314,865, filed on Mar. 17, 2010.

(51) Int. Cl.
  A61B 17/86 (2006.01)
  A61B 17/17 (2006.01)
  A61B 90/92 (2016.01)
  A61B 17/34 (2006.01)
  A61B 17/00 (2006.01)

(52) U.S. Cl.
  CPC .......... A61B 17/3472 (2013.01); A61B 17/84 (2013.01); A61B 17/842 (2013.01); A61B 17/8665 (2013.01); A61B 90/92 (2016.02); A61B 17/3421 (2013.01); A61B 2017/00004 (2013.01)

(56) References Cited

U.S. PATENT DOCUMENTS

| | | | |
|---|---|---|---|
| 4,119,091 A | 10/1978 | Partridge | |
| 4,185,624 A | 1/1980 | Gentile | |
| 4,535,764 A | 8/1985 | Ebert | |
| 4,796,612 A | 1/1989 | Reese | |
| 5,002,544 A | 3/1991 | Klaue et al. | |
| 5,151,103 A | 9/1992 | Tepic et al. | |
| 5,167,664 A | 12/1992 | Hodorek | |
| 5,167,665 A | 12/1992 | McKinney | |
| 5,217,462 A | 6/1993 | Asnis et al. | |
| 5,250,049 A | 10/1993 | Michael | |
| 5,269,784 A | 12/1993 | Mast | |
| 5,356,417 A | 10/1994 | Golds | |
| 5,498,265 A | 3/1996 | Asnis et al. | |
| 5,549,612 A | 8/1996 | Yapp et al. | |
| 5,616,144 A | 4/1997 | Yapp et al. | |
| 5,643,274 A | 7/1997 | Sander et al. | |
| 5,707,373 A | 1/1998 | Sevrain et al. | |
| 5,722,976 A | 3/1998 | Brown | |
| 5,921,986 A * | 7/1999 | Bonutti | A61B 17/0401 606/57 |
| 5,989,255 A | 11/1999 | Pepper et al. | |
| 5,997,538 A | 12/1999 | Asnis et al. | |
| 6,004,327 A | 12/1999 | Asnis et al. | |
| 6,013,083 A | 1/2000 | Bennett | |
| 6,200,318 B1 | 3/2001 | Har-Shai et al. | |
| 6,302,887 B1 * | 10/2001 | Spranza | A61B 17/861 411/338 |
| 6,309,393 B1 | 10/2001 | Tepic et al. | |
| 6,368,326 B1 * | 4/2002 | Dakin | A61B 17/8861 606/103 |
| 6,416,518 B1 | 7/2002 | DeMayo | |
| 6,514,274 B1 | 2/2003 | Boucher et al. | |
| 6,685,707 B2 | 2/2004 | Roman et al. | |
| 6,755,831 B2 | 6/2004 | Putnam et al. | |
| 6,761,722 B2 | 7/2004 | Cole et al. | |
| 6,786,909 B1 | 9/2004 | Dransfeld et al. | |
| 6,902,567 B2 | 6/2005 | Del Medico | |
| 6,918,912 B2 | 7/2005 | Seemann | |
| 6,942,668 B2 | 9/2005 | Padget et al. | |
| 6,971,995 B2 | 12/2005 | Rolnick et al. | |
| 7,225,813 B2 | 6/2007 | Easter | |
| 7,488,347 B1 * | 2/2009 | Goble | A61F 2/30756 623/18.11 |
| 7,615,069 B2 | 11/2009 | Paul | |
| 7,833,255 B2 | 11/2010 | Chow et al. | |
| 7,837,717 B2 * | 11/2010 | Deffenbaugh | A61B 17/683 606/281 |
| 8,282,674 B2 * | 10/2012 | Gelfand | A61B 17/8085 606/280 |
| 8,821,580 B2 | 9/2014 | DaSilva | |
| 9,028,547 B2 | 5/2015 | Lebeau et al. | |
| 9,101,426 B2 | 8/2015 | Forderer et al. | |
| 2002/0077659 A1 | 6/2002 | Johnson et al. | |
| 2002/0091391 A1 * | 7/2002 | Cole | A61F 2/0811 606/103 |
| 2002/0123750 A1 | 9/2002 | Eisermann et al. | |
| 2002/0161319 A1 | 10/2002 | Matsumoto et al. | |
| 2002/0188297 A1 | 12/2002 | Dakin et al. | |
| 2002/0192051 A1 | 12/2002 | LeVey et al. | |
| 2003/0078585 A1 | 4/2003 | Johnson et al. | |
| 2004/0116930 A1 | 6/2004 | O'Driscoll et al. | |
| 2004/0147928 A1 | 7/2004 | Landry et al. | |
| 2004/0153075 A1 | 8/2004 | Roger | |
| 2005/0015088 A1 | 1/2005 | Ringeisen | |
| 2005/0043742 A1 | 2/2005 | Bruneau et al. | |
| 2005/0080421 A1 | 4/2005 | Weaver et al. | |
| 2005/0085819 A1 | 4/2005 | Ellis et al. | |
| 2005/0149032 A1 | 7/2005 | Vaughen et al. | |
| 2005/0273104 A1 | 12/2005 | Oepen et al. | |
| 2006/0004367 A1 | 1/2006 | Alamin et al. | |
| 2006/0085000 A1 | 4/2006 | Mohr et al. | |
| 2006/0167393 A1 | 7/2006 | Bolla | |
| 2006/0271198 A1 | 11/2006 | McAfee | |
| 2007/0123883 A1 * | 5/2007 | Ellis | A61B 17/8076 606/326 |
| 2007/0213727 A1 | 9/2007 | Bottlang et al. | |
| 2007/0225715 A1 * | 9/2007 | Deffenbaugh | A61B 17/683 606/304 |
| 2007/0270852 A1 | 11/2007 | Tormala et al. | |
| 2007/0299448 A1 * | 12/2007 | Chin | A61B 17/7059 606/276 |
| 2008/0027360 A1 | 1/2008 | Smith | |
| 2008/0108997 A1 | 5/2008 | Berrevoets et al. | |
| 2008/0234754 A1 | 9/2008 | McCarthy et al. | |
| 2008/0281364 A1 | 11/2008 | Chirico et al. | |
| 2009/0012571 A1 | 1/2009 | Perrow et al. | |
| 2009/0048575 A1 | 2/2009 | Waters | |
| 2009/0138051 A1 | 5/2009 | Olms et al. | |
| 2009/0312802 A1 * | 12/2009 | DaSilva | A61B 17/8014 606/281 |
| 2009/0318977 A1 | 12/2009 | Di Giacomo et al. | |
| 2010/0004691 A1 | 1/2010 | Amato et al. | |
| 2010/0030276 A1 | 2/2010 | Huebner et al. | |
| 2010/0036431 A1 | 2/2010 | Haidukewyeh | |
| 2010/0121382 A1 | 5/2010 | Weiman | |
| 2010/0131012 A1 | 5/2010 | Ralph et al. | |
| 2010/0131013 A1 | 5/2010 | Ralph et al. | |
| 2010/0168799 A1 | 7/2010 | Schumer | |
| 2010/0331892 A1 | 12/2010 | Fell et al. | |
| 2011/0004252 A1 | 1/2011 | Velikov | |
| 2011/0313466 A1 | 12/2011 | Butler et al. | |
| 2012/0010662 A1 | 1/2012 | O'Neil et al. | |
| 2014/0277175 A1 | 9/2014 | Campbell et al. | |
| 2015/0094773 A1 | 4/2015 | Clasbrummel et al. | |

OTHER PUBLICATIONS

Acute Innovations, RibLoc, Rib Fracture Plating System, Technique Guide, Jul. 2008, pp. 1-2.

Devitt, "Blunt Thoriac Trauma: Assessment, Management, and Anaesthesia", Winterlude, 1995, 10 pages.

Wanek et al., "Blunt thoriac trauma: flail chest, pulmonary contusion, and blast injury", Critical Care Clinics 20, 2004, pp. 71-81.

Bastos, MD et al., "Flail Chest and Pulmonary Contusion", Thoracic and Cardiovascular Surgery, 2008, vol. 20, pp. 39-45.

Kadam et al., "Management of Chest Wall Injuries: A Comparison of Ventilatory and Non-Ventilatory Therapy", Indian J. Anaesth., 2003, 47 (2), pp. 100-104.

Engel et al., "Operative Chest Wall Fixation with Osteosynthesis Plates", The Journal of Trauma, vol. 58, No. 1, 2005, pp. 181-186.

Marasco et al., "Mode of Failure of Rib Fixation With Absorbable Plates: A Clinical and Numerical Modeling Study", The Journal of Trauma, vol. 68, No. 5, May 2010, pp. 1225-1233.

(56) References Cited

OTHER PUBLICATIONS

Dato et al, "Surgical management of flail chest", The Annals of Thoracic Surgery, vol. 67, 1999, pp. 1826-1827.
www.iconocast.com, "Surgical Stabilization of Severe Flail Chest", Jun. 14, 2005, 6 pages.
ClinicalTrails.gov archive, View of NCT00810251 on Dec. 17, 2008, "Efficacy of MatrixRIB Implants for Surgical Stabilization of Flail Chest Injuries", 3 pages.
Mohta et al., "Experiences with chest trauma: Where do we stand today", Indian J. Crit. CareMed, Jan.-Mar. 20006, vol. 10(1), pp. 25-28.
International Search Report and Written Opinion for Application No. PCT/US2010/040596, dated Sep. 1, 2010, 9 pages.
International Preliminary Report for Application No. PCT/US2010/040596, dated Jan. 12, 2012, 7 pages.
Extended European Search Report for Application No. 10794703.8, dated Jul. 14, 2014, 8 pages.
U.S. Office Action for U.S. Appl. No. 13/835,719, dated Jan. 7, 2016, 6 pages.
U.S. Office Action for U.S. Appl. No. 13/835,719, dated Mar. 24, 2016, 12 pages.
U.S. Office Action for U.S. Appl. No. 13/835,719, dated Aug. 10, 2017, 22 pages.
U.S. Office Action for U.S. Appl. No. 13/835,719, dated Apr. 12, 2018, 25 pages.

* cited by examiner

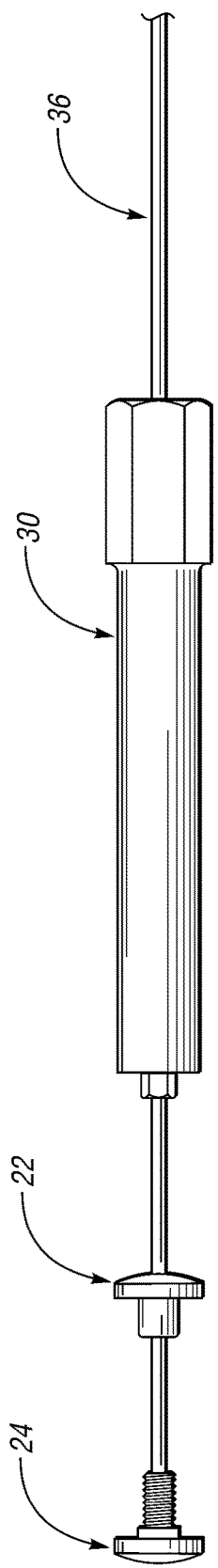
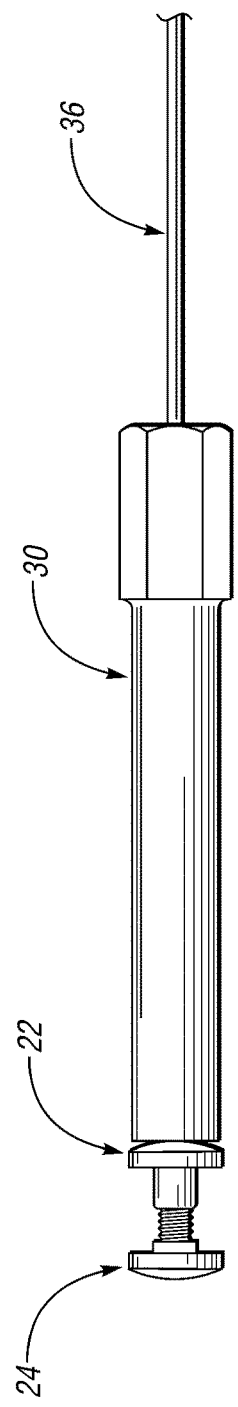
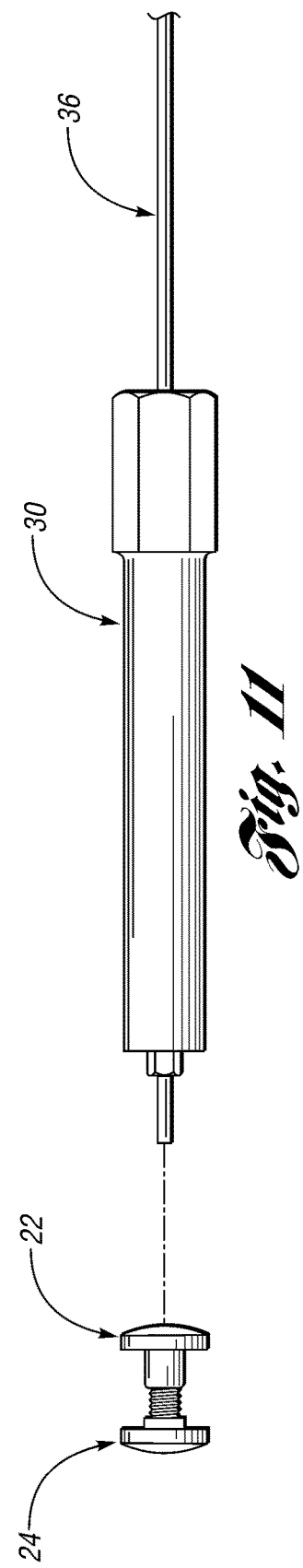
Fig. 9
Fig. 10
Fig. 11

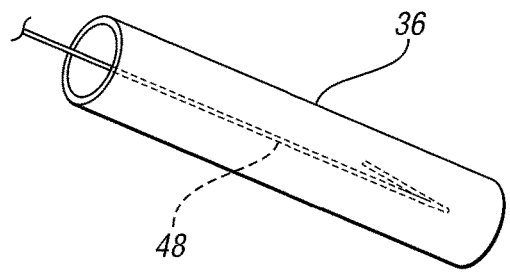
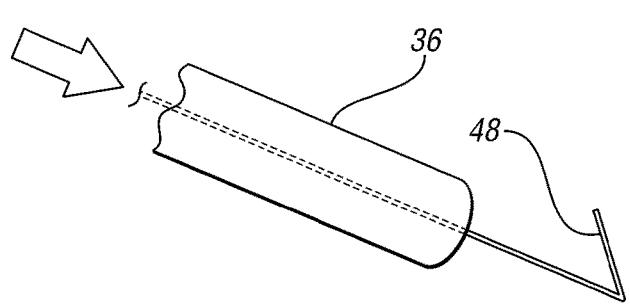
Fig. 25a    Fig. 25b
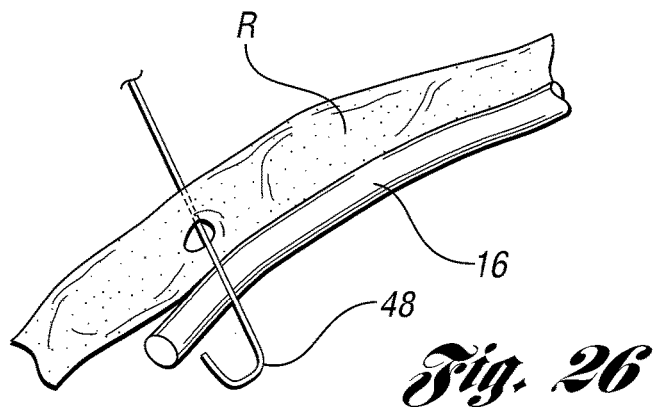
Fig. 26
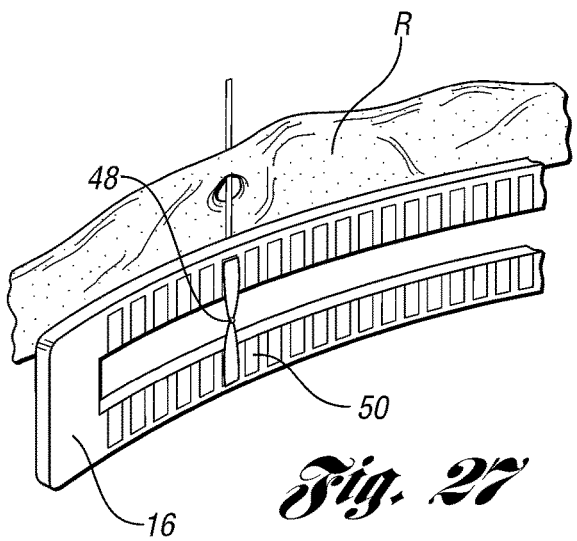
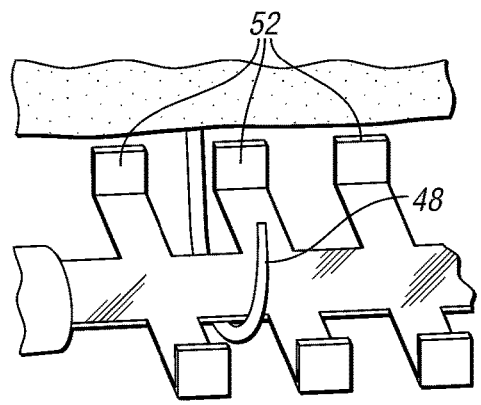
Fig. 27    Fig. 28

BONE REPAIR SYSTEM AND METHOD

CROSS-REFERENCE TO RELATED APPLICATIONS

This application is a divisional of U.S. application Ser. No. 15/433,499 filed Feb. 15, 2017, now U.S. Pat. No. 10,537,372, which is a continuation of U.S. application Ser. No. 14/252,064 filed Apr. 14, 2014, which is a divisional of U.S. application Ser. No. 12/825,967 filed Jun. 29, 2010, now U.S. Pat. No. 8,728,133, which claims the benefit of U.S. provisional Application No. 61/221,744 filed Jun. 30, 2009 and U.S. provisional Application No. 61/314,865 filed Mar. 17, 2010, the disclosures of which are incorporated in their entirety by reference herein.

TECHNICAL FIELD

This invention relates to a system and method for the repair of fractured or broken bones, such as ribs.

BACKGROUND

A flail chest is a condition that occurs when multiple adjacent ribs are broken, separating a segment of the chest wall so that it becomes detached from the rest of the chest wall and moves independently therefrom. This detached segment moves in the opposite direction as the rest of the chest wall, moving inward while the rest of the chest is moving outward and vice versa, creating "paradoxical motion" that increases the effort and pain involved in breathing.

Most rib fractures are treated conservatively using pain management and/or bracing techniques. Fractured ribs in a flail chest treated in such a manner may undergo progressive displacement during the healing phase, resulting in considerable deformity, volume loss, atelectasis, and chronic pain. Long-term problems of patients with flail chest injuries treated nonoperatively include subjective chest tightness, thoracic cage pain, and dyspnea.

Four categories of fixation devices for operative chest wall fixation have been utilized, namely plates, intramedullary devices, vertical bridging, and wiring. The results of these repair techniques are often less than desirable because of the difficulty in correctly locating the broken rib ends with one another. Stabilizing rib fractures is challenging because large incisions are typically needed to accommodate fixation, which leads to a more morbid procedure. In addition, ribs are narrow with a thin cortex that surrounds soft marrow, making reliable fixation problematic under conditions that include upwards of 25,000 breathing cycles per day, as well as coughing. Still further, there is risk of damage to the neurovascular bundle.

Currently, the surgery involves a significant operative procedure with mobilization of large chest wall flaps or open thoracotomy. The problems and risks of an operative approach include the surgical trauma itself and the loosening and migration of implants. The surgery involves a major incision through the muscle directly down to the ribs, which can have complications such as loss of muscle function, blood loss, and damage to surrounding vascular and neural tissue. The ribs that are to be fixed need to be adequately exposed in order to obtain a good placement of metal fixation plates. A wide incision is performed, and myocutaneous flaps may need to be raised to allow visualization of all segments. Posterior injuries are usually challenging due to the presence and required exposure of large muscle fibers (e.g., latissimus dorsi, trapezius, rhomboids, paraspinous muscles). The procedure utilized in current practice is typically at least three hours in length with an additional hour required for the closing of the surgical exposure.

BRIEF DESCRIPTION OF THE DRAWINGS

FIG. 9 is a side elevational view of a fastener assembly and drive tool according to another aspect of the present invention with a flexible rod passed therethrough;

FIG. 10 is a side elevational view of the drive tool engaged with the outer fastener;

FIG. 11 is a side elevational view of the engaged outer and inner fasteners and the flexible rod and drive tool removed;

FIGS. 25a and 25b are schematic representations of a fastener in a first position for insertion and second position for deployment, respectively, in accordance with an aspect of the present invention;

FIG. 26 illustrates a fastener engaging a reinforcing member according to an aspect of the present invention;

FIG. 27 illustrates another fastener engaging another reinforcing member according to an aspect of the present invention; and FIG. 28 depicts a bone plate with legs for receiving the fastener therebetween in accordance with another aspect of the present invention.

DETAILED DESCRIPTION

Figure 1:
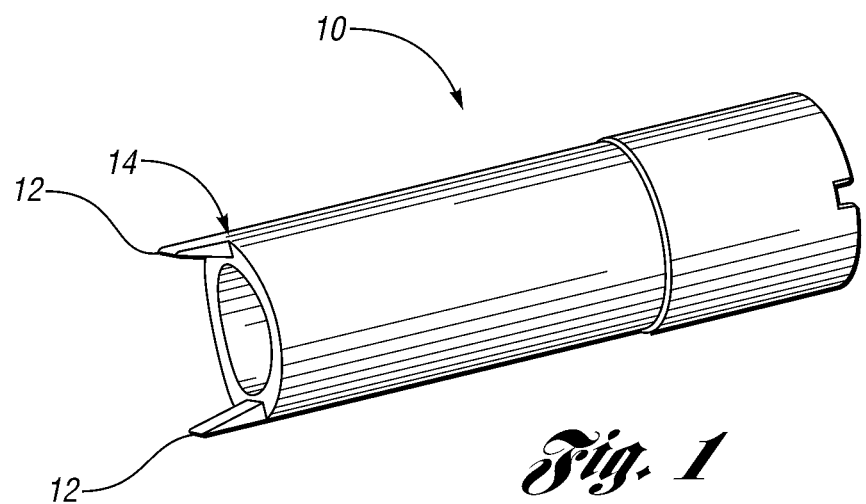
FIG. 1 is a perspective view of a trocar in accordance with an aspect of the present invention.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present invention provides a system and method for repairing fractured or broken bones, such as ribs. The system and method according to the present invention allow bone repair to be performed in a minimally invasive manner, thereby lessening patient recovery time. Although the system and method are shown and described herein as being applied to the repair of fractured ribs, it is understood that their application to the repair of other broken bones is fully contemplated. For example, the system and method according to the present invention may also be utilized for the minimally invasive repair of bone segments such as a fractured clavicle, fractured tibia, fractured pelvis, fractured spine, or fractured joint surface where there are displaced and/or multiple bone fragments that would otherwise require a large open surgical exposure to repair.

In overview, in accordance with an aspect of the present invention, fixation of bone segments such as fractured ribs includes the placement of tethered repair components through a percutaneous skin incision down to the bone and delivery of repair components into the pleural space. Assistance may be provided by a video-thoroscope, imaging technologies, or other minimally invasive observation method. The tethered repair components include a reinforcing member, such as a bone plate, and a fastener assembly, such as a screw and nut or other compressive fastener assembly, wherein the broken rib segment is stabilized by securing the bone plate against the rib with the fastener assembly. The bone plate may be attached to the rib on its internal surface, the side of the rib lining the pleural space. The tether, such as a cable or rod, serves to facilitate the procedure by guiding and providing control over the repair components, and to provide safety and efficiency for the surgeon.

The use of such means of rib fixation according to the present invention allows for the passage of fastener hardware through the central, thickest portion of the rib, thus minimizing the risk of inadvertent damage to the peripheral neurovascular anatomy. Further, the rib is a very small bone that typically has only a thin cortical shell or, in some cases, is comprised of largely cartilaginous material. Thus, a traditional repair utilizing typical bone screws has a significant chance of the screw loosening and thus the plate becoming loose over time.

A rib fracture repair can be performed in accordance with an aspect of the present invention utilizing one or more small (e.g., <15 mm) percutaneous incisions. A first incision may be utilized to percutaneously locate and drill holes for the passage of fasteners which allow for simultaneous capture and engagement with both inner and outer portions of the rib and mechanical interlock with the reinforcing member. A second incision allows for the percutaneous insertion of fasteners and reinforcing members to be placed against the rib via the pleural space. A third incision may be utilized to allow for thoracoscopic visualization of the fracture site. In the drawings provided herein, although not shown, it is understood that the patient's skin overlies the ribs R and the above-described incisions are made therethrough.

Figure 2:
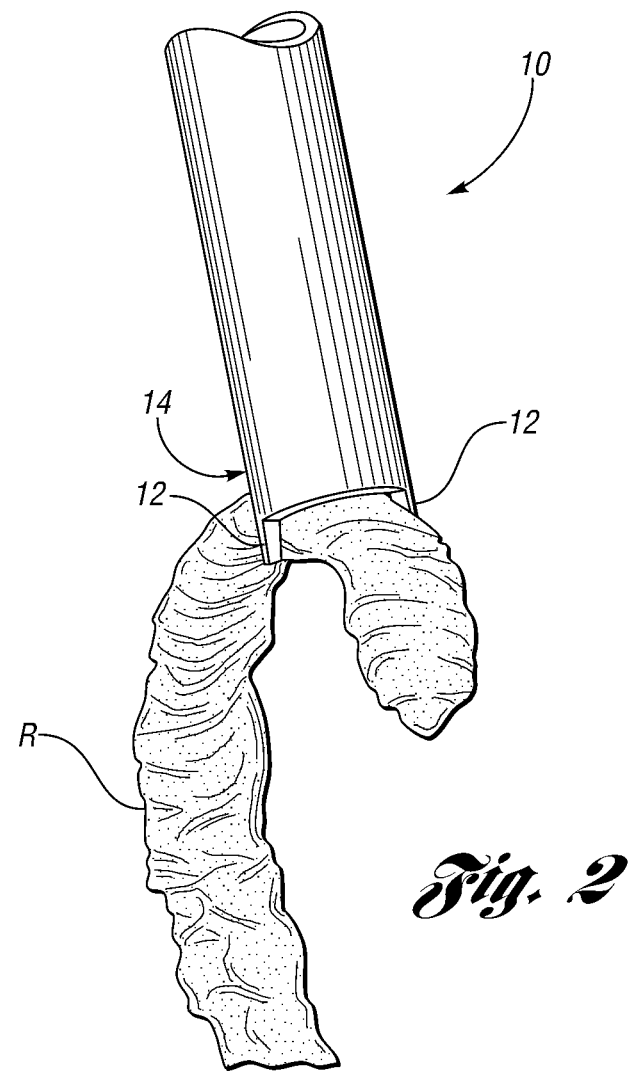
FIG. 2 is a schematic representation of the trocar engaged with a patient's rib.

With reference to FIGS. 1 and 2, in accordance with an aspect of the present invention, a trocar 10 may be percutaneously inserted through a skin incision (i.e., the first incision described above; not shown) and placed in contact with the rib R. Insertion of the trocar 10 assists in locating the rib R and is used to facilitate drilling of a hole through the rib R for affixing the reinforcing member to the rib R. The trocar 10 may be generally tubular or have an otherwise hollow configuration, and have a length capable of reaching the affected fracture site and engaging the bone in a controlled fashion. The trocar 10 may include two spaced spades or protrusions 12 at the engagement end 14 thereof to help orient the trocar 10 relative to the affected bone. The protrusions 12 may orient the trocar 10 centrally over a width of the rib R or in a manner such that another specific location on the bone and the long orientation of the bone can be positively identified by the surgeon. Further, the protrusions 12 may actively engage the bone in such a manner as to cause a positive lock to the bone, thus maintaining the position of the trocar 10 relative to the bone and fracture site throughout the surgery. In one embodiment, the protrusions 12 may be diametrically spaced on the trocar engagement end 14.

During the surgical repair, the protrusions 12 may be positioned along the sides of the rib R as illustrated in FIG. 2, thus generally centering the trocar 10 over the rib R. Accordingly, the trocar 10 will locate a subsequently inserted drill guide generally centrally over the width of the rib R such that the hole drilled for receipt of the fastener assembly will be generally located in the center of the rib R as measured from side to side. According to an aspect of the present invention, a navigated trocar may be employed.

Figure 3:
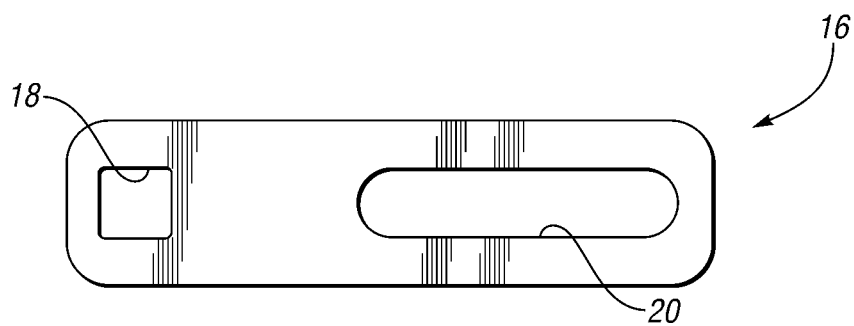
FIG. 3 is a top plan view of a bone plate in accordance with an aspect of the present invention.
Figure 18:
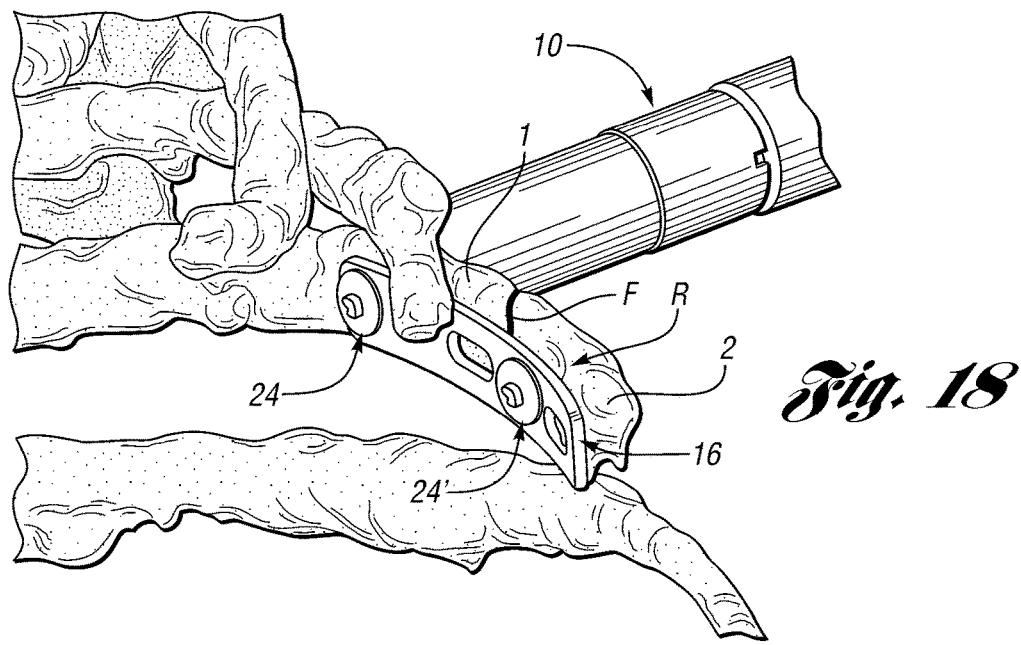
FIG. 18 is a schematic representation of the bone plate secured in position on the internal surface of the rib.

Turning to FIG. 3, an exemplary reinforcing member, bone plate 16, is depicted which may be constructed from an appropriate material such as, but not limited to, titanium, stainless steel, polymer, ceramic or a bio-resorbable material or combinations thereof. The bone plate 16 includes at least two openings to accept a fastener assembly that allows the bone plate 16 to be securely fastened in position. In one embodiment, the bone plate 16 includes a hole 18 at one end at least one elongated slot 20 at the other end. In accordance with an aspect of the present invention, the hole 18 may either be square or have another not-round shape. The bone plate 16 can be constructed with any combination of holes 18 and elongated slots 20 for achieving the desired stability. With reference to FIG. 18, a non-limiting example includes a single hole 18 and three elongated slots 20. Providing a bone plate 16 with one or more elongated slots 20 allows the hole locations in the bone to be more flexible along each slot 20 for bone plate location, thus less precision is required. This is especially beneficial when positioning a bone plate 16 along the more curved elements of the ribs.

Figure 19:
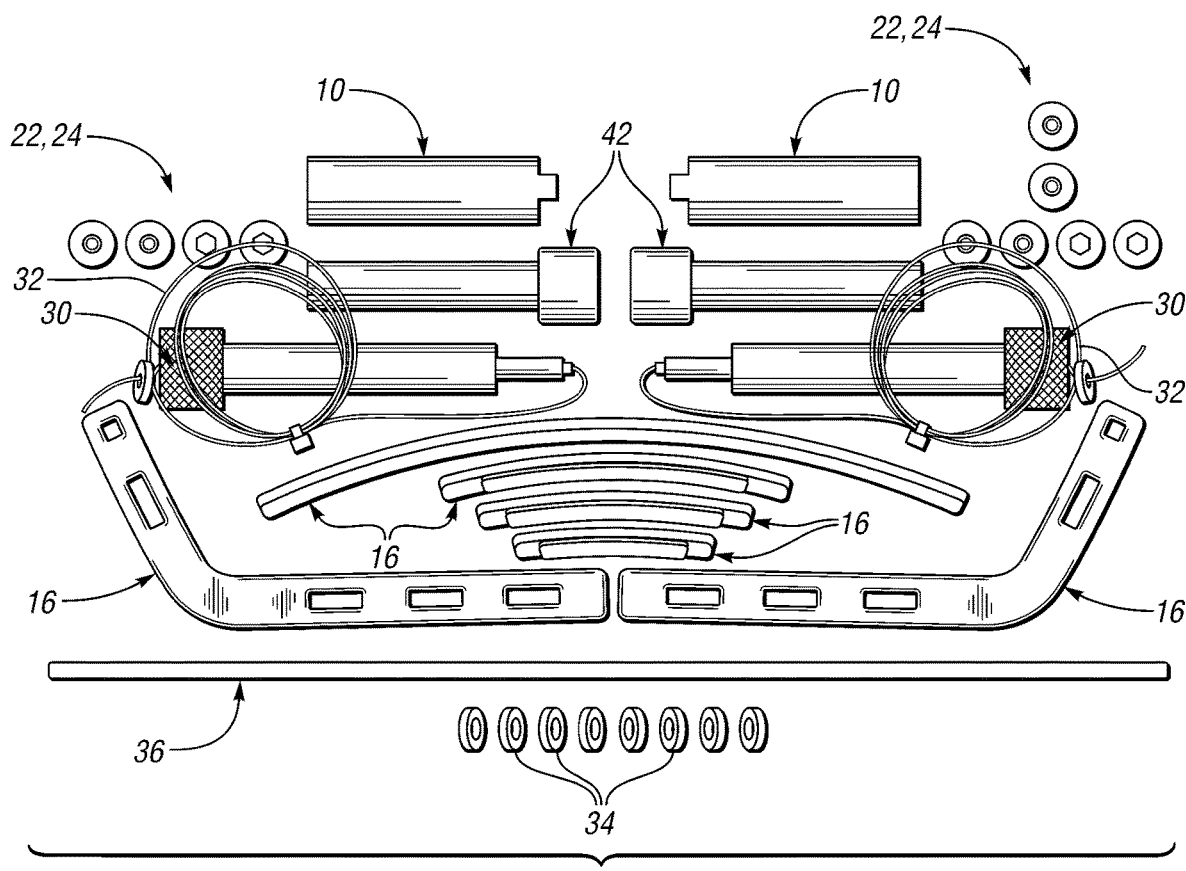
FIG. 19 is a top plan view of a surgical kit in accordance with an aspect of the present invention.

For the type of repair described herein, according to one non-limiting aspect of the present invention, the bone plate 16 may be approximately 2-20 mm in width, or more particularly 8-12 mm in width. The length of the bone plate 16 is as needed, but according to one non-limiting aspect of the present invention may range from 40-400 mm. The thickness of the bone plate 16 can be uniform or variable, such as providing greater thickness near the middle of the bone plate 16 to enhance stiffness or to tailor the stiffness to a specific level, such as to match the particular section of the rib bone. According to one non-limiting aspect of the present invention, bone plate thickness may range from 0.25-4 mm. The bone plate 16 may be generally linear or may include angled portions (FIG. 19). Of course, it is understood that the bone plates 16 described herein may have any shape and are not limited to any of the above dimensions, and may instead appear as cables, rods, or other shapes.

The bone plate 16 may be generally planar, or may instead be curved (FIG. 19). The bone plate 16 can be curved in a planar fashion or twisted in a non-planar, curvilinear fashion in order to conform to the more difficult shapes of certain ribs, such as those found in the most anterior and posterior portions of the rib cage. Curvature desired of the bone plate 16 can be based on CT or other noninvasive diagnostic imaging techniques, or through physical measurement of the rib cage at the time of surgery. Curvature in the bone plate 16 can be established at the time of manufacture, thus providing a library of shapes appropriate to the approximate shape(s) of the rib(s) to be repaired, or the bone plate 16 could be custom bent at the time of the surgery in the operating room.

In one embodiment, a CT of the patient's rib cage may be performed prior to surgery. The CT data may then be fed into a specially designed analytical software program, wherein the ideal shape of the bone plate 16 may be determined based on the shape of the existing healthy portions of the patient's rib cage and anatomical atlases. A determination may be made, with a combination of this analytical software and surgeon input, to establish the ideal shape of the bone plate 16 required to repair the fracture site. A computer-controlled bending or template machine can be utilized to mold or shape an existing generically sized bone plate 16 into a specific patient-matched plate, prior to or at the time of the surgery, thereby minimizing the time required to complete the surgical repair.

According to an aspect of the present invention, the bone plate 16 can be coated with a substance to assist in reducing inflammation. According to another aspect of the present invention, an adhesive may be applied to the bone plate 16 to adhere it permanently or temporarily to the rib.

Figure 4:
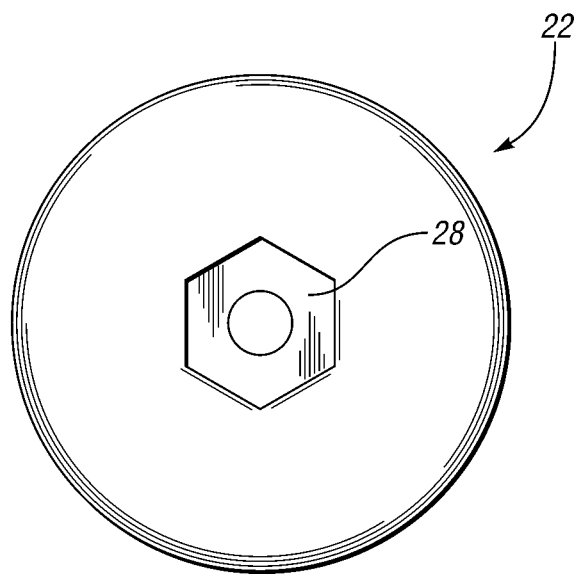
FIG. 4 is a top plan view of an outer fastener in accordance with an aspect of the present invention.
Figure 5:
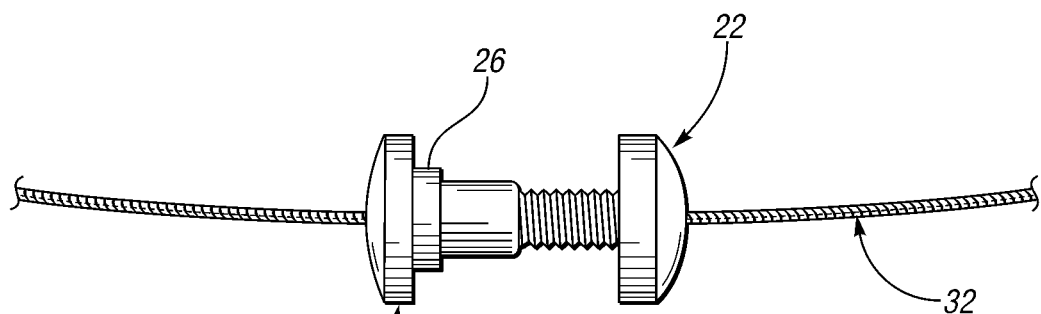
FIG. 5 is a side elevational view of a fastener assembly in accordance with an aspect of the present invention with a cable passed therethrough.

With reference to FIGS. 4 and 5, first, or outer 22, and second, or inner 24, fasteners according to an aspect of the present invention are shown, wherein the outer and inner fasteners 22, 24 each include a longitudinal channel (not shown) in order to receive a tether, such as a cable or rod, therethrough. Outer and inner fasteners 22, 24 engage to form a fastener assembly that secures the bone plate 16 to the rib. In one embodiment, the outer fastener 22 may be a threaded screw and the inner fastener 24 may be a nut, although it is understood that other fasteners are also contemplated. For example, fasteners such as screws with machine threads, tapered threads, rivets, adhesively joined, and other such positive engagement type fasteners may be utilized.

The inner fastener 24, which resides in the pleural space, may have a portion, such as shoulder 26, shaped to facilitate engagement with and prevent rotation of the fastener assembly when engaging the holes 18 or slots 20 of the bone plate 16. In one embodiment, a square or other non-round shaped shoulder 26 may be used. Such a configuration is beneficial since the surgeon may not have direct physical access to the inner fastener 24 in order to hold the inner fastener 24 securely while tightening the outer fastener 22 as described below. The inner fastener 24 may also be engaged mechanically to the bone plate 16 prior to its insertion. The outer fastener 22 may include an engagement port 28 for engagement by a drive tool 30 (FIG. 6) to accomplish tightening of the engaged fastener assembly. Of course, it is also contemplated that a drive tool could be configured to be inserted into the pleural space and engage with and tighten the inner fastener 24, or that the outer fastener 22 could include a shoulder as described above.

Figure 6:
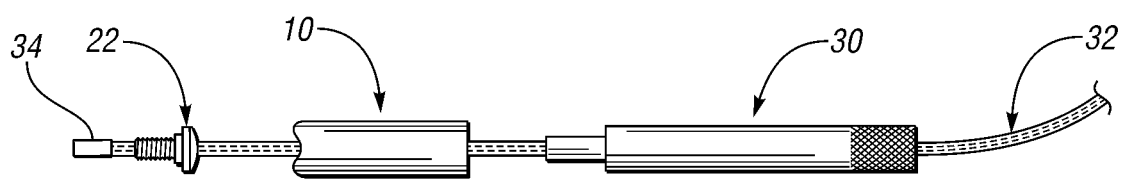
FIG. 6 is a side elevational view of an outer fastener, trocar, and drive tool in accordance with an aspect of the present invention with a cable passed therethrough.
Figure 7:
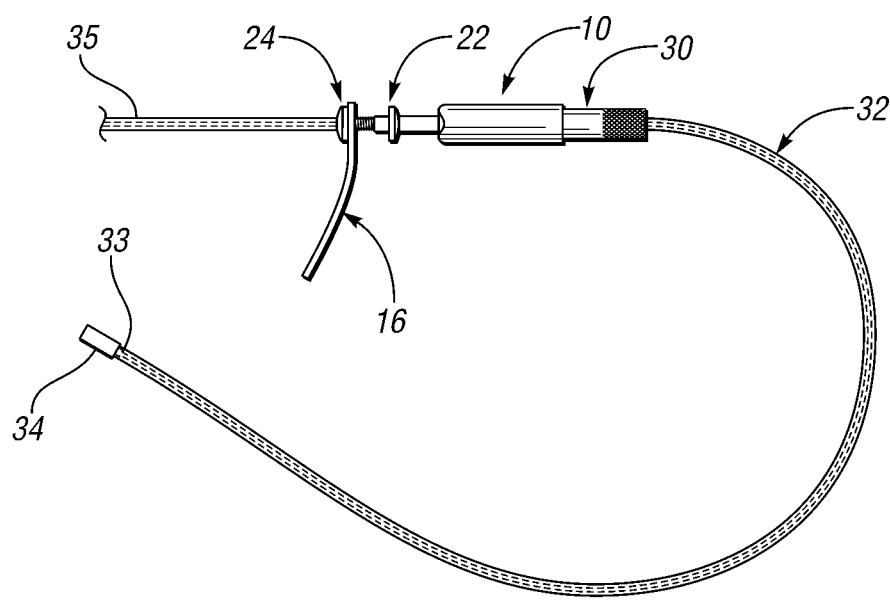
FIG. 7 is a side elevational view of a bone plate and inner fastener combined with the components of FIG. 6.
Figure 8:
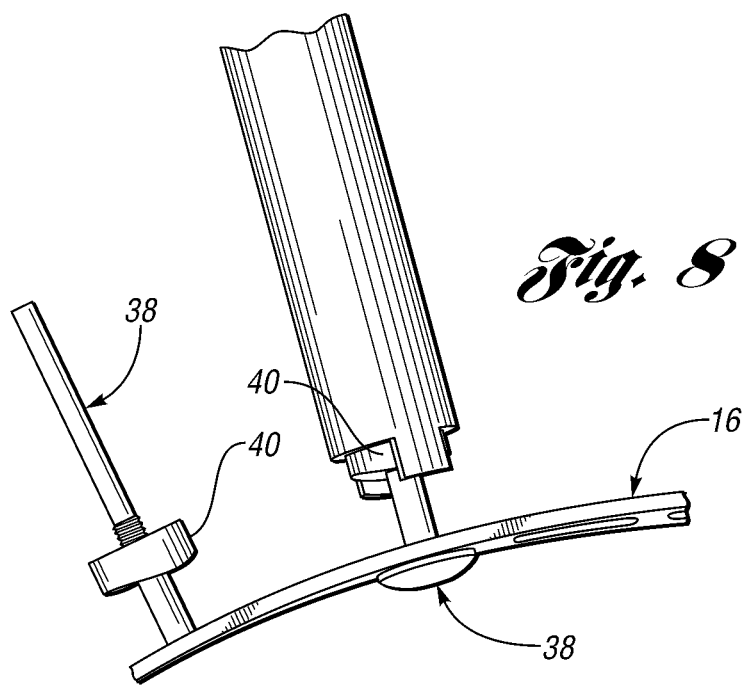
FIG. 8 is a schematic representation of an alternative fastener assembly according to an aspect of the present invention.

As shown in FIGS. 5-7, each of the fastener assembly 22, 24, the trocar 10, the drive tool 30, and the bone plate 16 are configured to have a tether or guide member, such as a cable 32, passed therethrough, wherein the cable 32 also passes through a hole drilled in the bone in order to locate and guide the bone plate 16 and fasteners 22, 24. In one embodiment, each cable 32 or other tether may be colored or have another identifying feature, and may include a secure grommet 34 at its proximal 33 and distal 35 ends to maintain control of the location of the repair components.

Instead of a cable 32, a flexible rod 36, such as made of plastic or metal, may be used as depicted in FIGS. 9-11. The rod 36 may be used to pass through inner and outer fasteners 22, 24 and the drive tool 30 as shown in FIG. 9, along with passing through the other components and the drilled bone, performing a guide function for the repair components as with the cable 32 described above. Rod 36 includes proximal 37 and distal 39 ends, wherein a distal end 39 of the rod 36 may be threaded or utilize other mechanical means for securing the inner fastener 24 thereto. Of course, it is understood that grommets 34 could be instead used with the rods 36, and that the cable distal end 35 could instead be threaded. Along the flexible rod 36, the drive tool 30 engages the outer fastener 22 (FIG. 10) and tightens it to the inner fastener 24 (FIG. 11). If further safety is desired, the rod 36 can also be made hollow to accept a centrally located wire or cable in case the rod 36 fails. Use of a larger diameter flexible rod 36, as compared with a cable 32, may allow the surgeon to exert more tensile force on the bone plate 16 and fastener assembly 22, 24 without undo risk of breakage. A portion of the rod 36 may also be used as an integral portion of the final fastener assembly.

In another embodiment, a snare-type tether may be used that can loop or otherwise engage the reinforcing member 16 to facilitate locating the reinforcing member 16 against the rib. Such a snare-type tether can also act as both as a fastener and guidance mechanism, such that it is contemplated that the inner fastener 24 could be eliminated. In addition, the tether distal end may mechanically engage the reinforcing member 16 for pulling the reinforcing member 16 into the body and securing to a fastener, such as with a bayonet connection.

In accordance with another aspect of the present invention, an alternative to the threaded fastener assembly is the use of an inner fastener comprising a grooved member 38, inserted through the bone from the inside as depicted in FIG.

8. While under location and tensile control by the cable 32 or rod 36, an outer fastener comprising a rapid connecting ratcheting nut 40 may be pushed down over the grooved member 38. In this embodiment, the nut motion is only vertical relative to the bone plate 16, thus measures for preventing fastener rotation are unnecessary. The underside of the nut 40 may have a concave shape such that it has a more intimate fit with the outer surface of the rib and can distribute the compressive loads of the nut 40 more evenly to the rib.

In a further variation, a fastener assembly may be utilized that is adhesively bonded together while under compressive loading, applied from a tool capable of pulling the inner fastener 24 and bone plate 16 together with the outer fastener 22. While holding the assembly under the compressive loading, thus securing the bone plate 16 to the rib, an adhesive may be applied either alongside the cable 32 or from within a hollow core of the rod 36. Once the adhesive is set, the cable 32 or rod 36 can be removed, provided they are coated with a release or non-stick coating. If such a coating is not provided, the cable 32 or rod 36 can be cut off, such as near the top of the outer fastener 22.

Simultaneous with the adhesive approach, or in combination with the all-mechanical approach of the fastener assembly, the hollow rod 36 or fastener assembly 22, 24 could be used to deliver bone cement to the fracture site while the fracture is in a reduced state. The fastener assembly could be removed upon setting of the bone cement or be left in place. If the fastener assembly is made of bio-resorbable materials, the fastener assembly could be left in place to resorb over a period of time, ultimately leaving no sign of the original fracture repair.

Figure 12:
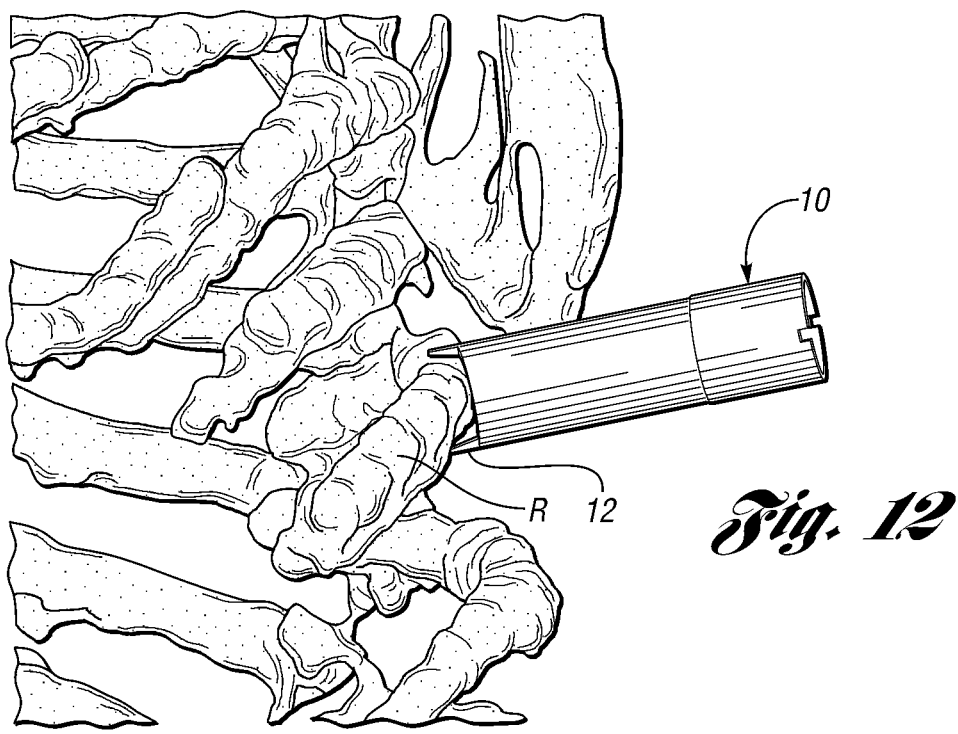
FIG. 12 is a schematic representation of a trocar in accordance with the present invention engaged with a patient's rib.

With reference now to FIGS. 12-18, a method for repair of a bone fracture F in accordance with the present invention will be described wherein a first bone segment 1 is fixed to a second bone segment 2. The fracture site to be repaired may be initially identified radiographically or via ultrasound and, at the time of surgery, through video-assisted viewing through a thorascope (not shown). The site may be palpated externally and confirmed internally to identify the size and location of the fracture and any displacement of the rib segments. A percutaneous incision (e.g., the first incision described above) may be made directly over an intact, stable portion of the rib followed with a blunt dissection of the tissue down to the bone itself. As shown in FIG. 12, according to an aspect of the present invention, the trocar 10 may be used to locate the rib R by passing the trocar 10 through the soft tissue down to the bone. The trocar 10 may be positioned generally centrally over the rib by assuring that the protrusions 12 are positioned along the sides of the rib R. The trocar 10 may also actively engage the bone in such a manner as to cause a positive lock to the bone, thus maintaining the position of the trocar relative to the bone and fracture site throughout the surgery.

Figure 13:
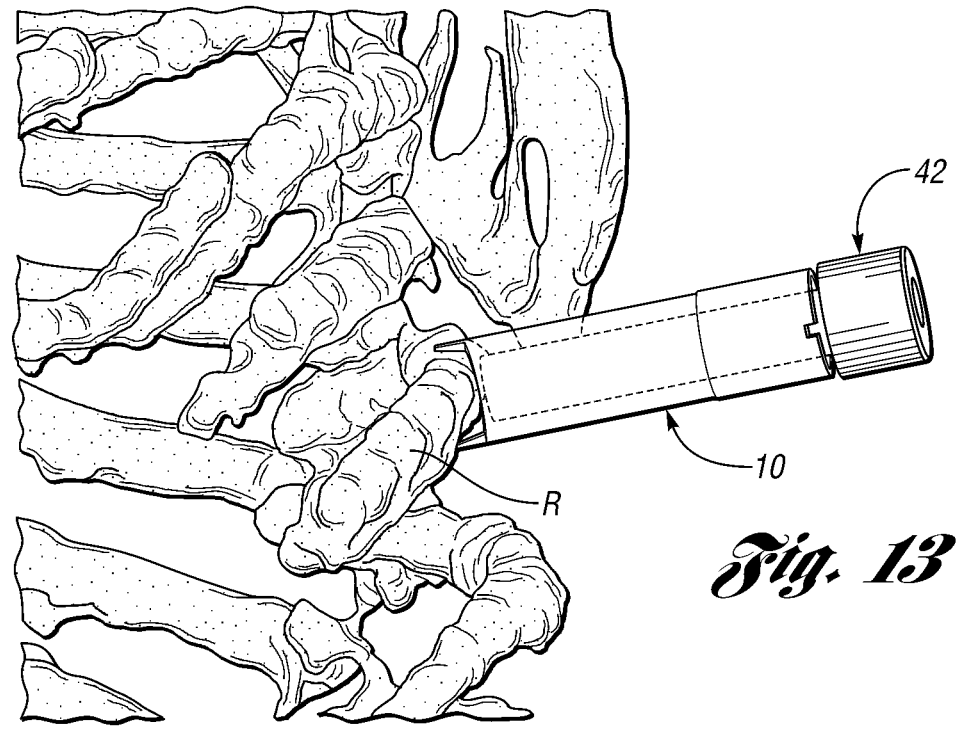
FIG. 13 is a schematic representation of a drill guide inserted into the trocar.

Referring to FIG. 13, according to an aspect of the present invention, a drill guide 42 may be placed inside the trocar 10 and used to facilitate the drilling of a hole through the bone, wherein the hole will receive the fastener assembly 22, 24. In one embodiment, a drill, such as a cannulated wire drill, may be used to facilitate passage of the cable 32 or flexible rod 36 through the rib R to the other side of the fractured bone. In some situations, the rod 36 or cable 32 may be passed through the drilled hole on its own after removal of the drill. Drilling may occur under direct visualization using a thorascope. Furthermore, utilization of fluoroscopy or another real-time imaging method may aid the surgeon in locating, repositioning and fixing in place the displaced rib segments.

Figure 14:
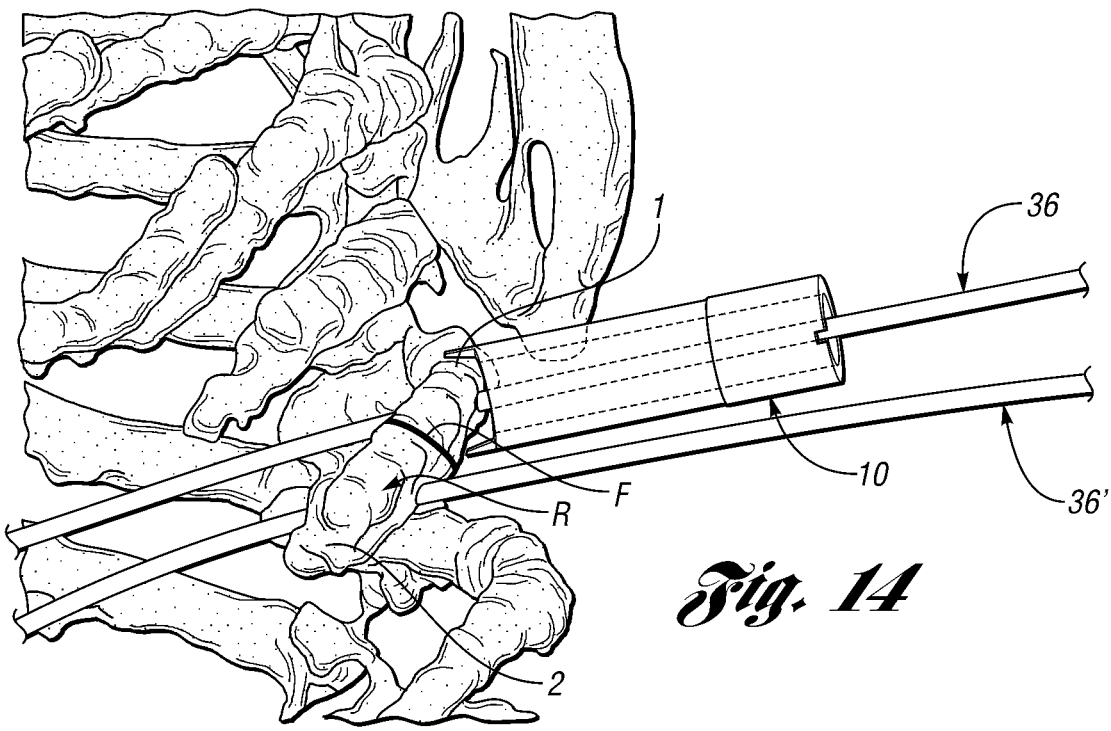
FIG. 14 is a schematic representation of rods passed through the trocar and newly formed holes in the rib.
Figure 15:
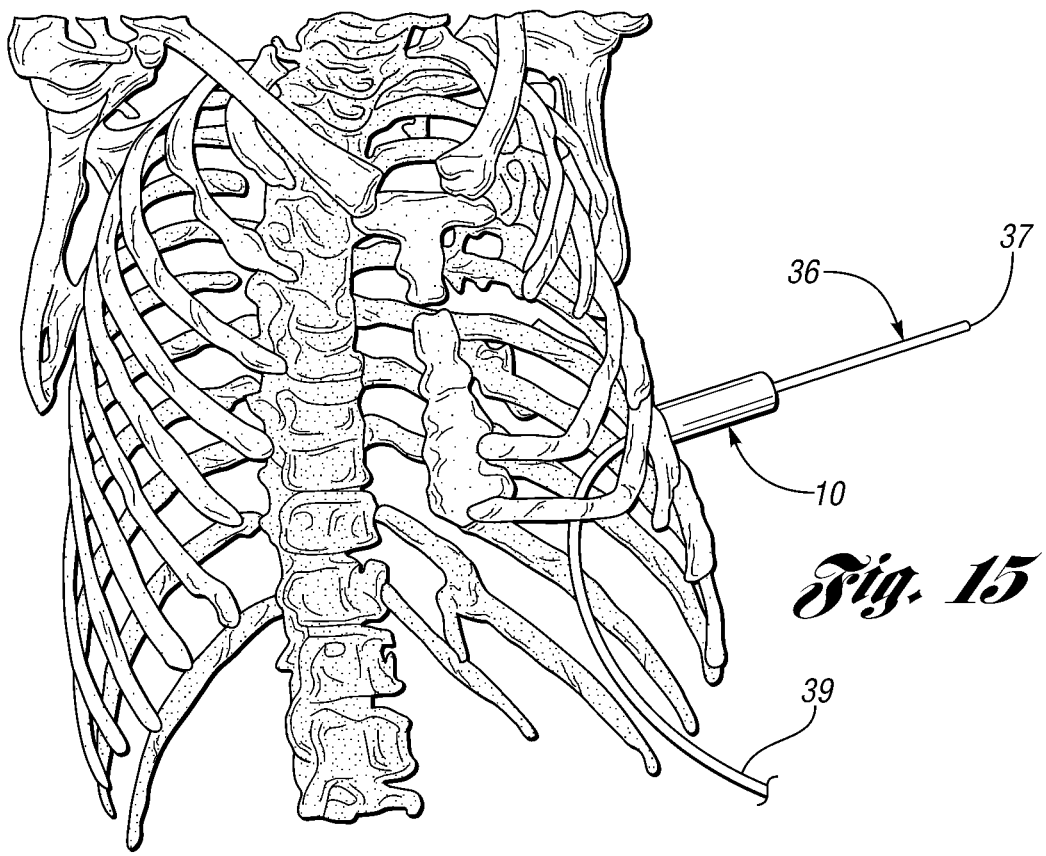
FIG. 15 is a schematic representation of a rod being passed through the rib and back out of the chest cavity.

As shown in FIG. 14, according to an aspect of the present invention, the rod 36 (or cable 32 or other tether) is passed through the drill guide 42, and through the created hole in the rib R and into the pleural space. A first rod 36 and a second rod 36' are depicted. The entrance into the pleural space may be visualized with a video thorascope. The cable or rod distal end 35, 39 is grabbed, such as with a grasping instrument (not shown), and withdrawn through the second incision referenced above and outside of the chest cavity (FIG. 15). As an alternative, the threaded rod or cable may be externally guided such that its placement and path through the pleural space can be entirely guided by the surgeon without the need for thorascopic instruments to grab them from the inside, similar to the manner in which an endoscope is manipulated. This externally guided rod or cable assembly can also have the video guidance built into it, thus eliminating any need for a thorascopic incision port (i.e., the third incision referenced above). At this point in the surgery, both the proximal 33, 37 and distal 35, 39 ends of the cable 32 or rod 36 are visible from outside of the patient's body.

Once inserted through the rib, both the cable 32 and the threaded rod 36 can also be used to reduce the fracture through mechanical manipulation of the bone ends. The surgeon is able to pull on the displaced bone directly from outside of the chest cavity without the need for a larger exposure while simultaneously aligning the bone plate 16 and fasteners 22, 24 into final position. While applying such correcting force, the surgeon is able to tighten or otherwise fasten the bone plate 16 into its final corrective position. Since the method according to the present invention allows for access to both sides of the rib simultaneously, in certain circumstances it may also be desirable to pass a tether, such as a cable, from one drilled rib hole to another in order to pull the bones together. In this instance, a grommet or other stop can be placed on the proximal or distal end of the tether to prevent the tether from pulling through the holes when force is applied to the end of the tether opposite the stop.

Figure 16:
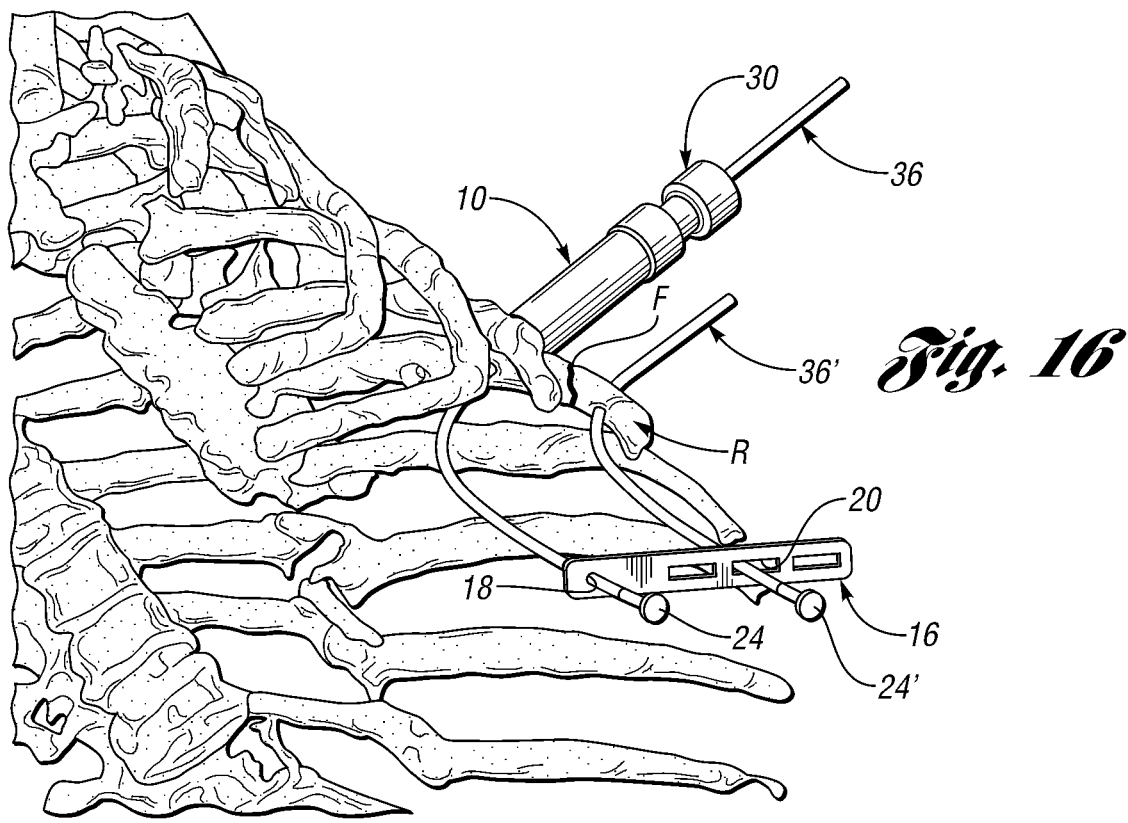
FIG. 16 is a schematic representation of the drive tool inserted into the trocar and the inner fastener and bone plate being passed through the opposite ends of the rods into engagement with the internal surface of the rib.

FIG. 16 illustrates placement of the bone plate 16 and first and second inner fasteners 24, 24' onto the first and second flexible rods 36, 36', respectively, in accordance with an aspect of the present invention. When a cable 32 is used, once the cable 32 is drawn through the abdominal wall, the bone plate 16 may first be passed over the cable distal end 35 followed by the inner fastener 24. A grommet 34 (or a wire button or the like) may be used to secure the distal end 35, wherein the grommet 34 should be large enough to prevent the bone plate 16 and inner fastener 24 from becoming disengaged from the cable 32. When a rod 36 is used, once the rod 36 is drawn through the abdominal wall, the bone plate 16 may first be passed over the rod distal end 39. The inner fastener 24 may then be threaded or otherwise secured onto the distal end 39 for positive control over the bone plate 16 and fastener assembly. Once the repair components have been secured to the cable 32 or rod 36, the components are ready to be drawn back into the thoracic cavity for placement against the desired rib segment pulled and guided by the cable 32/rod 36.

The procedure may be repeated for subsequent drilled holes, typically on the other side of the bone fracture F, wherein a differently identifiable (e.g., color or other means of identification) cable 32 or rod 36 may be used in order to identify the particular location through the rib R. As described above, the bone plate 16 may include one or more elongated slots 20 through which additional cables 32/rods 36 may be passed. An initial distance measurement between drilled points on the bone may be made of the external (e.g., first) incision points. That distance may be further confirmed by the use of a thorascopically deployed measuring instrument so that the inner distance between holes can be made. This measurement provides information as to the curvilinear and/or straight configuration of the rib cage, and provides the surgeon with an accurate assessment of the relative drilled bone position once the fracture site has been properly reduced. The use of a combination of holes 18 and slots 20 on the bone plate 16 reduces the need for exact hole placement on the rib by the surgeon, as the final position of the fasteners 22, 24 on the bone plate 16 is adjustable due to use of the slots 20. This configuration accommodates imprecise drilled hole and fastener placement through the rib.

Figure 17:
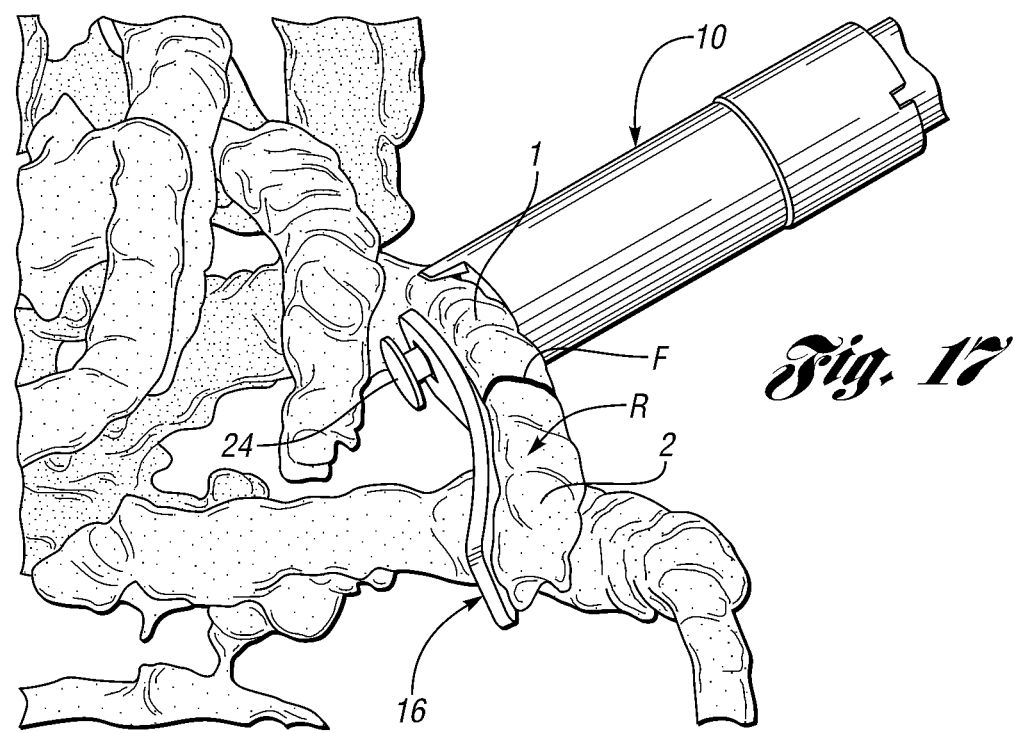
FIG. 17 is a schematic representation of the inner fastener and bone plate being secured into position on the rib via tightening of the outer fastener with the drive tool.

Once the desired number of cables 32/rods 36 has been brought out through the instrument port (e.g., second incision), the bone plate 16 may be fed onto the cables 32/rods 36 in the proper orientation. In one embodiment, the end of the bone plate 16 where the single square hole 18 is located may be utilized against the stable rib portion. The bone plate 16 and inner fastener 24 may then be drawn into the chest cavity and pleural space and, with possible video and thorascopic assistance, the bone plate 16 may be positioned near the site of the rib fracture to be repaired while the cables 32/rods 36 are slowly drawn through the drilled holes in the rib R as illustrated in FIG. 17. The use of two or more cable or rod assemblies at one time will assure the proper orientation of the plate and fastener assemblies once pulled back into and against the internal surface of the chest cavity.

In accordance with an aspect of the present invention, once the drill guide 42 is removed from the trocar 10, the outer fastener 22 may be moved into position along the cable 32/rod 36 through the drilled hole into the bone, into engagement with the inner fastener 24, and secured thereto with the drive tool 30 (FIG. 18). In one embodiment, the fastener assembly 22, 24 inserted through the hole 18 of the bone plate 16 may be tightened first, followed by the fastener assembly 22, 24 inserted through the slot 20 since less alignment between the rib hole and bone plate opening is required with the slot configuration. Tension may be applied to the cable 32/rod 36 by the surgeon, thus drawing the inner fastener 24 into position with the bone. Once the inner fastener 24 engages the bone plate 16, the outer fastener 22 may be tightened with the drive tool 30 until the desired level of torque and tightness has been reached. The drive tool 30 may engage the engagement port 28 of the outer fastener 22 in order to rotate the outer fastener 22 and secure it to the inner fastener 24. In one embodiment, the inner fastener 24 may be prevented from turning by its square shoulder 26 engaging in a square hole 18 on the bone plate 16. Of course, other methods of securing the outer and inner fasteners 22, 24 together are also fully contemplated.

In one embodiment, a washer (not shown) may be used under the outer fastener 22 to aid in distributing the load between the outer fastener 22 and the bone. The washer may be concave shaped (on the bone-mating side), oriented to fit saddle-like over the rib, to attempt to further reduce localized stresses on the bone. The washer may also be enhanced with a deformable component to reduce the localized bone stresses even further.

If repositioning of the rib segment is required to reduce the fracture, then the use of a device, such as a gimlet, can be used to help facilitate the relocation of the broken segment while the fastener assemblies 22, 24 are tightened. The cable 32 or rod 36 can also can act to facilitate alignment of bone segments for reduction of the fracture site, since the bone segment can be pulled with the cable 32 or rod 36 and re-located as required once the inner fastener 24 and the bone plate 16 are engaged with the inner side of the bone. In addition to the use of the cable 32 or rod 36 to facilitate reduction of the fracture site, a pressure applying device, such as a balloon, can be used as part of the thorascope assembly or in conjunction with it to apply pressure against the pleura, and thus the ribs, and position them into a conforming shape. This will help reduce the fractured ribs if necessary, and hold the ribs in that position until the fasteners 22, 24 are tightened.

Once all of the fastener assemblies 22, 24 are tightened and the surgeon is comfortable with the location, tightness, stability and other parameters such as reduced position of the bones, the rod 36 may be unscrewed or otherwise detached from the inner fastener 24 and removed, thus completing the repair. In the case of the cable 32, the grommet 34 on either end 33, 35 may be cut and the cable 32 withdrawn from the chest cavity. Standard layer closure utilizing resorbable sutures followed by a local rib block (e.g., with Marcaine) may be used to complete the surgical steps. Visual and tactile feedback of the repair should be considered sufficient, and the procedure may then be repeated for other drilled locations.

According to an aspect of the present invention, the bone plate 16 may be part of a system including components that are flexible or deformable, such that the components can be delivered or deployed into the body or working location in a first configuration, and then change configuration, either actively or passively, into a second configuration once inserted into the pleural space. These components may include, for example, plates, washers, cables, wires, fasteners, or parts of these components. A deformable plate component may be longitudinally rolled, coiled, or compressed in preparation for delivery and then wholly or partially deployed or manipulated while inside the pleural space. The components may be partially deployed so that part of the component may assume one function while another part may serve another function. The deformable components may be steered, guided, or directed into a shape, location, or configuration as part of the fixation system in accordance with the present invention.

Figure 20:
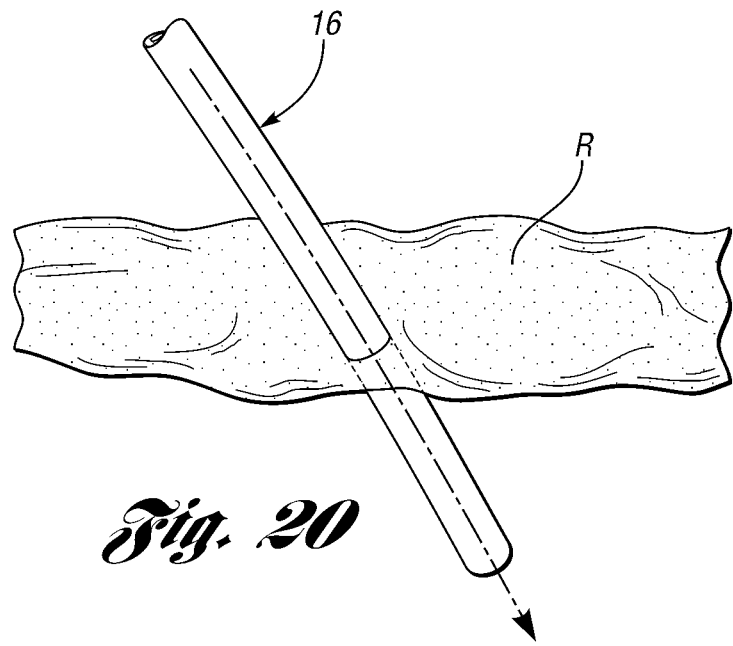
FIG. 20 is a perspective view of a deformable plate component according to an aspect of the present invention being inserted through the rib in a rolled configuration.
Figure 21:
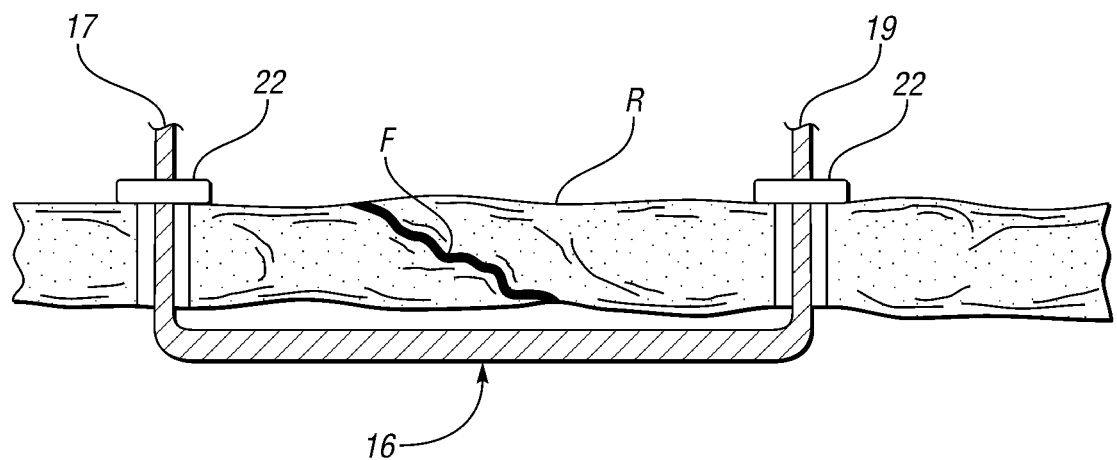
FIG. 21 is a side cross-sectional view of a deformable plate component inserted through and between two adjacent holes in the rib.
Figure 22:
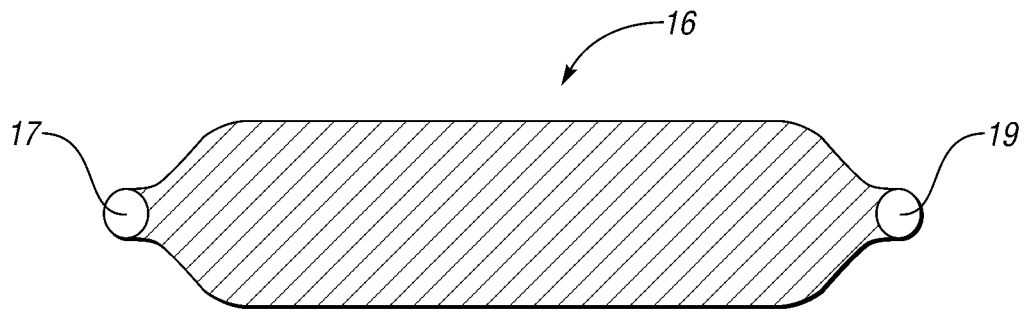
FIG. 22 is a top plan view of a deformable plate component in a deployed configuration in accordance with an aspect of the present invention.

In one embodiment, a deformable plate component 16 may be inserted while in a first configuration, such as a rolled shape, into one drilled rib hole (FIG. 20), into the pleural space and then fed back out, across the fracture area F, and out of the pleural space through another drilled rib hole (FIG. 21). The area of the bone plate 16 between the holes on the pleural side may then be at least partially deployed into a second configuration, such as a non-round shape (FIG. 22). The end portions 17, 19 of the deformable plate 16 that pass through the rib may still be maintained in their original round shape and secured in place while under tension with an appropriate fastener 22, such as a unidirectional push lock. The ends 17, 19 of the deformable plate 16 may then be trimmed to the appropriate length.

Bone plates 16 can be additive to affect their length. For example, the bone plate 16 may be a smaller, individual portion of a modular system of coupling or interlocking bone plates that, once inserted and placed into general position, can be locked into final position through the tightening of fasteners 22 and 24. In one embodiment, the ends of one plate can engage with the next plate in line, such as in an overlapped toothed fashion, thus allowing for shaping of the plate while it is already in the pleural space and providing for more accurate final positioning by the surgeon.

Figure 23:
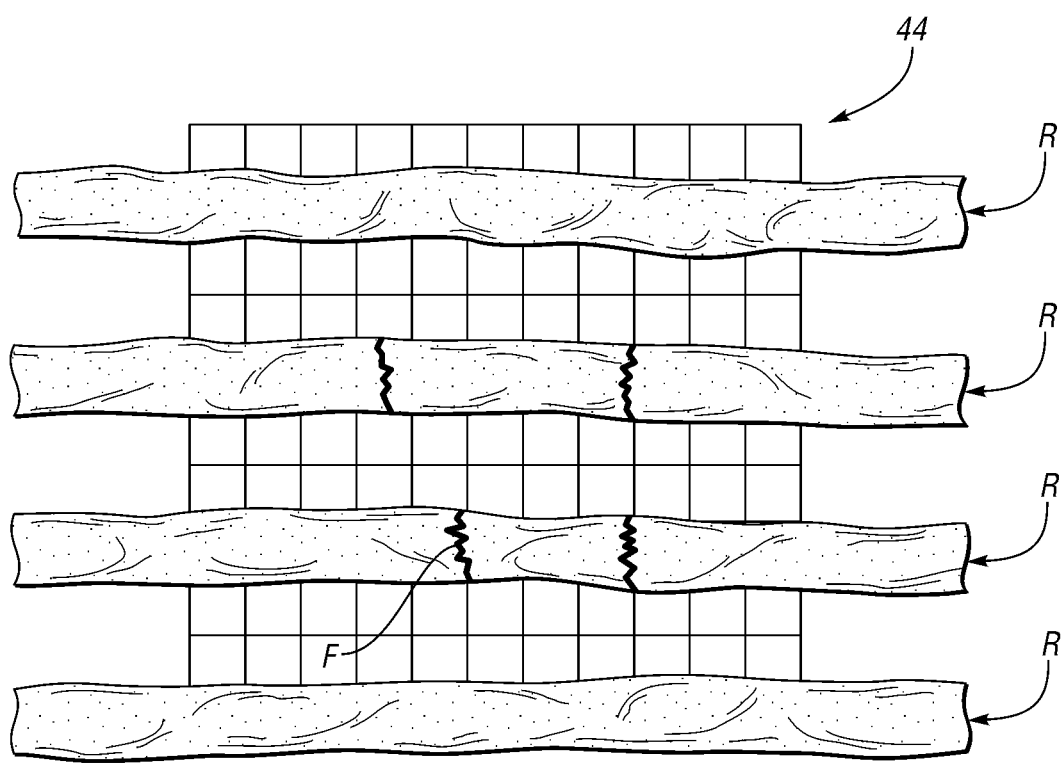
FIG. 23 is an illustration of a composite reinforcing structural component or patch disposed across a plurality of ribs according to an aspect of the present invention.

In one embodiment, the bone plate 16 may be made of a reinforcing mesh or fabric of fibers combined with a resin matrix to form a composite reinforcing structural component or patch 44 as illustrated in FIG. 23. This patch 44 can be applied to the general area of the fracture F, extending beyond the fracture area to areas of non-fracture. Further, the patch 44 can be simultaneously applied across several spaced apart ribs R at one time as shown, thus allowing for a single reinforcing member for a multiple rib fracture site. The composite patch 44 can be joined adhesively to the pleural side of the repair across the entire surface, can be joined mechanically to the ribs, or a combination of both joining methods. The patch 44 can be supplied, while in an uncured or otherwise pliable state, to the pleural space in one shape for initial engagement of the bone segment, and then delivered and placed into final position, cured, bonded, or otherwise fastened to the pleural underside of the ribs.

Figure 24:
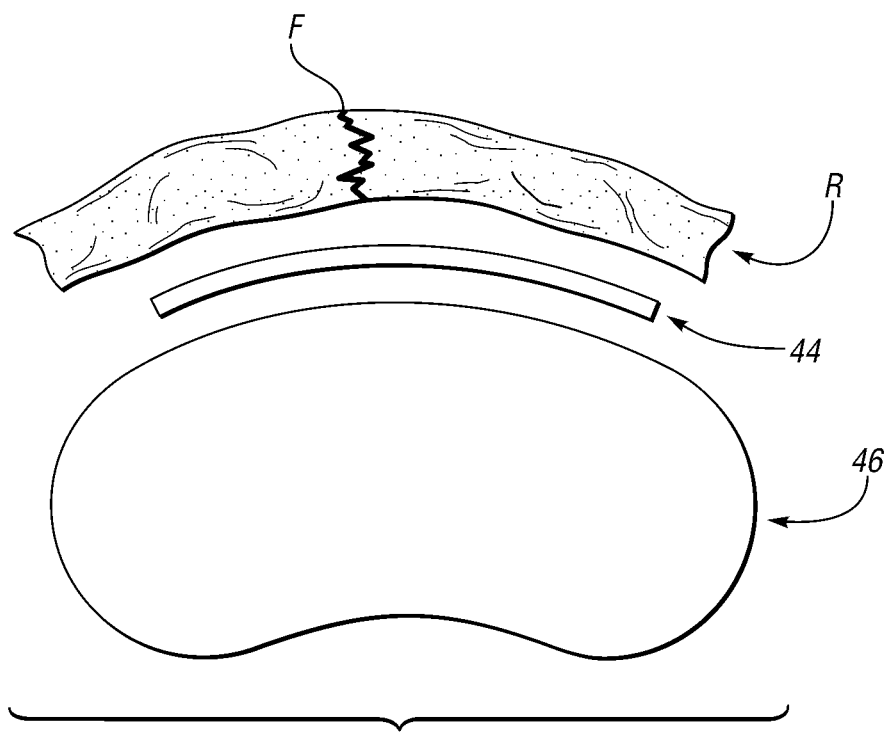
FIG. 24 is a side elevational view of a patch engaging a rib with assistance from a pressure applying device such as a balloon in accordance with an aspect of the present invention.

As an example of the above, a deformable patch 44 may be rolled, coiled, or compressed in preparation for delivery and then wholly or partially deployed or manipulated while inside the pleural space. Prior to curing or bonding to the pleura, the patch may further be steered, guided, or directed into a shape, location, or configuration as part of the fixation system according to the present invention. The patch may be positioned into correct placement with external manipulation via the aforementioned cables 32 or rods 36, or entirely through a thorascopic-only assisted and directed placement. In the example of thorascopic-only assisted and directed placement, a pressure applying device 46, such as a balloon, can be used as part of the thoracope assembly or in conjunction with it. As shown in FIG. 24, the pressure applying device 46 may be used to deploy the patch 44 against the pleura, position it into a conforming shape, reduce the fractured ribs if necessary, and hold the patch 44 in that position until the patch 44 is cured. In this manner, the patch 44 may either be adhesively bonded to the pleural lining and, if necessary, additionally mechanically attached to the ribs via the aforementioned fasteners and fastening methods. The pressure applying device 46 and thorascope (not shown) may then be removed and the repair will be complete.

As a primary means of fixation or if additional fasteners are desired, they can be added through the aforementioned means. Alternatively, with the bone plate 16 in the correct position and at least partially secured in place, additional fasteners may be placed through the bone plate 16 via the inside of the chest cavity by using an internally deployed drilling instrument that passes a drill, cable, rod or other tethering method through to the external portion of the rib cage. The fasteners used via such a reversed method can be similar to those fasteners described earlier. Alternatively, the fasteners can be of a blind type such that once the drill, cable or rod 36 is passed through the rib to the outside with the fastener 48 housed therein for insertion (FIG. 25*a*), the fastener 48 can be externally pushed, internally pulled down, or otherwise deployed (FIG. 25*b*) through the rib, through the bone plate 16 and through the application of outward tension, engage the plate 16 through the deployment of wings, hooks, arms or any other positive engagement means with the bone plate 16 (FIGS. 26 and 27) and secured in place by applying a counter locking mechanism, such as a push nut or threaded nut against the external portion of the rib bone (not shown). FIG. 26 depicts a fastener 48 engaging a cable or rod type reinforcing member 16, while FIG. 27 depicts a fastener 48 engaging a bone plate 16 which includes areas 50 for receiving the fasteners 48. In another embodiment illustrated in FIG. 28, the bone plate 16 may have legs 52 and the fastener 48 may be received and interlock between the legs 52, wherein the legs 52 may also have tabs for bone anchoring.

Any or all of the components described herein for completing the bone repair in accordance with an aspect of the present invention can be assembled for ease of use as a surgical kit as shown in FIG. 19. A tray can be provided where the components can be conveniently and securely positioned for ease of access and use during a surgery.

The system and method described herein allow for the rapid fixation of broken rib segments with minimal blood loss (e.g., a reduction of 80-90%), required surgical time (e.g., a reduction of 50-75%), and reduced post-operative pain and discomfort for the patient. Disruption of the surrounding musculature, soft tissue, cartilage, periosteum and neural structures is significantly reduced when compared to conventional surgical techniques. Once the surgery begins, each repair will typically take less than 10 minutes. This differs significantly from the current techniques which are quite lengthy, utilize a wide exposure, require large muscle dissection and often have a complicated recovery. Patient satisfaction with the repair should be high due to the absence of prominent hardware, minimal post-operative recovery time and the minimal nature of the incisions.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of percutaneously fixing a first bone segment to a second bone segment in a body of a patient, comprising:
   drilling a first hole through the first bone segment and a second hole through the second bone segment;
   feeding a first tether through the first hole and a second tether through the second hole, each tether having a proximal end and a distal end;
   withdrawing the first and second tether distal ends from the body while the first and second tether proximal ends have not passed through the first and second bone segments, respectively;
   passing a reinforcing member onto the first and second tether distal ends, the reinforcing member having at least a first opening and a second opening, wherein the reinforcing member includes a patch comprising a fiber mesh and resin matrix;
   pulling the reinforcing member into engagement with the first and second bone segments guided by the tethers; and
   securing the reinforcing member to the first bone segment and to the second bone segment to fix the first bone segment to the second bone segment.

2. The method of claim 1, wherein securing the reinforcing member includes adhesively joining the patch to a pleural side of the first and second bone segments.

3. The method of claim 1, further comprising deploying the patch against the bone segments using a pressure applying device.

4. The method of claim 1, wherein the first bone segment and the second bone segment are rib bone segments.

5. The method of claim 1, further comprising making a first percutaneous incision drilling the holes in the bone segments and a second percutaneous incision for passing the reinforcing member onto the tether distal ends.

6. The method of claim 1, wherein the patch is secured to the first bone segment with a first fastener assembly through the first hole and the first opening and to the second bone segment with a second fastener assembly through the second hole and the second opening.

7. The method of claim 6, wherein each tether distal end is threaded for receiving a portion of the first or second fastener assembly thereon.

8. The method of claim 6, wherein the first fastener assembly includes a first inner fastener and a first outer fastener, and the second fastener assembly includes a second inner fastener and a second outer fastener.

9. The method of claim 8, wherein securing the first and second fastener assemblies includes feeding the first inner fastener onto the first tether distal end and the second inner fastener onto the second tether distal end subsequent to passing the reinforcing member, and feeding the first outer fastener onto the first tether proximal end and feeding the second outer fastener onto the second tether proximal end.

10. The method of claim 8, further comprising pulling the tether proximal ends to draw the first inner fastener into engagement with the first outer fastener and to draw the second inner fastener into engagement with the second outer fastener.

11. The method of claim 1, further comprising withdrawing the first and second tethers from the body following securing the reinforcing member to the bone segments.

12. The method of claim 1, further comprising placing a stop member on each tether distal end subsequent to feeding the reinforcing member thereon.

13. The method of claim 1, wherein passing the reinforcing member includes inserting the reinforcing member into the body in a first configuration and then at least partially deploying the reinforcing member to a second configuration once inserted.

14. The method of claim 1, further comprising inserting a blind fastener through at least one of the first and second holes and engaging the reinforcing member by deploying positive engagement means from the blind fastener.

* * * * *